US010792060B2

(12) United States Patent
Batchelor et al.

(10) Patent No.: US 10,792,060 B2
(45) Date of Patent: Oct. 6, 2020

(54) INSTRUMENT WITH A CONTROLLED JAW MOVEMENT

(71) Applicant: GYRUS ACMI, INC., Southborough, MA (US)

(72) Inventors: Kester J. Batchelor, Mound, MN (US); Riyad Moe, Madison, WI (US); Huisun Wang, Maple Grove, MN (US); Laura B. Eliason, Salem, SC (US)

(73) Assignee: Gyrus Acmi, Inc., Southborough, MA (US)

( * ) Notice: Subject to any disclaimer, the term of this patent is extended or adjusted under 35 U.S.C. 154(b) by 200 days.

(21) Appl. No.: 15/902,113

(22) Filed: Feb. 22, 2018

(65) Prior Publication Data

US 2018/0263644 A1    Sep. 20, 2018

Related U.S. Application Data

(60) Provisional application No. 62/471,087, filed on Mar. 14, 2017.

(51) Int. Cl.
*A61B 17/29* (2006.01)
*A61B 17/28* (2006.01)
*A61B 18/14* (2006.01)

(52) U.S. Cl.
CPC ........ *A61B 17/2816* (2013.01); *A61B 17/282* (2013.01); *A61B 18/1445* (2013.01); *A61B 18/1447* (2013.01); *A61B 2017/2936* (2013.01); *A61B 2017/2944* (2013.01); *A61B 2018/145* (2013.01); *A61B 2018/1455* (2013.01)

(58) Field of Classification Search
CPC ........ A61B 17/2816; A61B 2017/2936; A61B 2017/2926; A61B 18/1445; A61B 18/1447; A61B 17/28; A61B 17/29; A61B 2017/2932; A61B 2017/2933; A61B 2017/2934; A61B 2017/2937; A61B 2017/2938; A61B 2017/2939; A61B 2017/2912; A61B 2017/2913; A61B 2017/2915; A61B 2017/2916
See application file for complete search history.

(56) References Cited

U.S. PATENT DOCUMENTS

| 5,431,674 A | 7/1995 | Basile et al. |
| 5,478,351 A | 12/1995 | Meade et al. |
| 5,509,922 A | 4/1996 | Aranyi et al. |

(Continued)

FOREIGN PATENT DOCUMENTS

| EP | 0584787 A1 | 3/1994 |
| WO | 2008/005411 A2 | 1/2008 |

*Primary Examiner* — Eric J Rosen
*Assistant Examiner* — Mohammed S Adam
(74) *Attorney, Agent, or Firm* — Schwegman Lundberg & Woessner, P.A.

(57) ABSTRACT

An instrument includes a hand piece, a pair of jaws, and an actuator. The jaws extend from the hand piece. Each jaw includes a proximal portion and a distal portion. The actuator is in communication with both the hand piece and the pair of jaws. Movement of the actuator causes the jaws to move from an open configuration to a closed configuration. During the move from the open configuration to the closed configuration, the jaws undergo a translational movement followed by a first non-translational movement.

17 Claims, 7 Drawing Sheets

(56) References Cited

U.S. PATENT DOCUMENTS

| | | | |
|---|---|---|---|
| 5,749,893 A | 5/1998 | Vidal et al. | |
| 5,849,022 A | 12/1998 | Sakashita et al. | |
| 6,024,750 A | 2/2000 | Mastri et al. | |
| 6,238,414 B1* | 5/2001 | Griffiths | A61B 17/29 606/205 |
| 6,458,130 B1 | 10/2002 | Frazier et al. | |
| 6,585,735 B1* | 7/2003 | Frazier | A61B 18/1445 606/51 |
| 6,964,662 B2 | 11/2005 | Kidooka | |
| 7,101,373 B2* | 9/2006 | Dycus | A61B 18/1445 606/51 |
| 7,678,117 B2 | 3/2010 | Hinman et al. | |
| 7,699,835 B2 | 4/2010 | Lee et al. | |
| 7,736,363 B2 | 6/2010 | Watanabe | |
| 8,496,682 B2 | 7/2013 | Guerra et al. | |
| 8,529,437 B2* | 9/2013 | Taylor | A61B 17/29 600/141 |
| 8,568,443 B1* | 10/2013 | Jackman | A61B 17/00 606/157 |
| 8,663,270 B2* | 3/2014 | Donnigan | A61B 17/29 227/60 |
| 8,709,035 B2 | 4/2014 | Johnson et al. | |
| 8,795,274 B2 | 8/2014 | Hanna | |
| 8,939,975 B2 | 1/2015 | Twomey et al. | |
| 8,968,311 B2 | 3/2015 | Allen, IV et al. | |
| 9,168,050 B1* | 10/2015 | Peine | A61B 17/2816 |
| 9,216,030 B2* | 12/2015 | Fan | A61B 17/29 |
| D748,787 S* | 2/2016 | Windgassen | D24/143 |
| 9,320,523 B2 | 4/2016 | Shelton, IV et al. | |
| 2003/0065358 A1* | 4/2003 | Frecker | A61B 17/29 606/205 |
| 2005/0165429 A1* | 7/2005 | Douglas | A61B 17/08 606/157 |
| 2005/0273085 A1 | 12/2005 | Hinman et al. | |
| 2006/0047278 A1* | 3/2006 | Christian | A61B 18/1442 606/41 |
| 2006/0052777 A1 | 3/2006 | Dumbauld | |
| 2006/0271042 A1 | 11/2006 | Latterell et al. | |
| 2008/0015575 A1* | 1/2008 | Odom | A61B 18/1445 606/51 |
| 2009/0054894 A1 | 2/2009 | Yachi | |
| 2009/0112254 A1* | 4/2009 | Yates | A61B 18/14 606/207 |
| 2009/0209991 A1* | 8/2009 | Hinchliffe | A61B 17/1608 606/170 |
| 2010/0057085 A1 | 3/2010 | Holcomb et al. | |
| 2011/0184404 A1* | 7/2011 | Walberg | A61B 18/1445 606/33 |
| 2011/0251612 A1* | 10/2011 | Faller | A61B 18/1445 606/52 |
| 2011/0301592 A1* | 12/2011 | Kerr | A61B 17/29 606/41 |
| 2012/0022584 A1* | 1/2012 | Donnigan | A61B 17/29 606/206 |
| 2013/0085494 A1* | 4/2013 | Weisenburgh | A61B 17/0469 606/41 |
| 2013/0296922 A1* | 11/2013 | Allen, IV | A61B 18/1445 606/205 |
| 2014/0100600 A1 | 4/2014 | Kendrick | |
| 2014/0107697 A1* | 4/2014 | Patani | A61B 17/12 606/208 |
| 2015/0066022 A1* | 3/2015 | Shelton, IV | A61B 18/082 606/41 |
| 2015/0105821 A1* | 4/2015 | Ward | A61B 17/29 606/206 |
| 2015/0148801 A1 | 5/2015 | Shahlaie et al. | |
| 2015/0209103 A1 | 7/2015 | Artale et al. | |
| 2015/0305796 A1* | 10/2015 | Wang | A61B 18/1445 606/52 |
| 2015/0331443 A1* | 11/2015 | Lamser | G05G 5/005 74/532 |
| 2016/0270807 A1* | 9/2016 | Worrell | A61B 17/2816 |
| 2016/0367239 A1* | 12/2016 | Mumaw | A61B 17/0469 |
| 2019/0247112 A1* | 8/2019 | Allen, IV | A61B 18/1445 |

* cited by examiner

INSTRUMENT WITH A CONTROLLED JAW MOVEMENT

FIELD

These teachings relate to an instrument, and more particularly to an instrument with controlled jaw movements.

BACKGROUND

Forceps are plier-like instruments that have opposing jaws. The jaws can be used during a medical procedure to effect an anatomical feature, such as a vessel or tissue. For example, a vessel or tissue can be positioned between the gripping sections of the opposing jaws, and the jaws can be used to move, grip, grasp, push, pull, cut, dissect and/or otherwise effect the vessel or tissue. Some forceps also include electrosurgical capabilities for electrically effecting an anatomical feature.

The jaws of the forceps can be moved between an open configuration and a closed configuration, where an anatomical feature can be gripped. In the closed configuration of a typical forceps instrument, gripping forces at a proximal portion of the jaws tend to be higher than gripping forces at a distal portion of the jaws. In some instances, an anatomical feature located at the proximal portion of these jaws may be damaged from the higher gripping forces. Moreover, higher gripping forces at the proximal portion of these jaws may undesirably push the anatomical feature along a length of the jaws and then "squirt" the anatomical feature from distal end thereof.

Opportunities exist for improving known forceps. For example, it may be desirable to have an instrument for effecting an anatomical feature without damaging the anatomical feature. It may be desirable to have an instrument for effecting an anatomical feature without the anatomical feature moving or "squirting off" the distal end of the jaws. Some examples of known instruments are disclosed in U.S. Pat. Nos. 5,626,607, 7,736,363, 8,663,270, in U.S. Patent Application Publication Numbers 2005/0273085, 2006/0271042, 2009/0054894, and in European Patent Application Publication Number EP2554135, the disclosures of which are all hereby incorporated by reference in their entirety.

SUMMARY

These teachings provide an instrument, comprising a hand piece; a pair of jaws; and an actuator. The pair of jaws extend from the hand piece. Each of the jaws include a proximal portion and a distal portion. The actuator is in communication with both the hand piece and the pair of jaws. Movement of the actuator causes the pair of jaws to move from an open configuration to a closed configuration. During the move from the open configuration to the closed configuration, the pair of jaws undergo a translational movement followed by a first non-translational movement.

These teachings also provide an instrument, comprising a hand piece; a pair of jaws; and an actuator. The pair of jaws extend from the hand piece. Each of the jaws include a proximal portion and a distal portion. The actuator is in communication with both the hand piece and the pair of jaws. Movement of the actuator affects a translational movement of the pair of jaws. Movement of the actuator also affects a first non-translational movement of the pair of jaws. The first non-translational movement occurs when the pair of jaws are closer together than during the translational movement.

These teachings further provide an instrument, comprising a hand piece; an introducer; a pair of jaws; an actuator; a first constraint; a second constraint; and a third constraint. The introducer extends from the hand piece. The pair of jaws extend form the introducer. The pair of jaws comprise a first jaw and a second jaw. The actuator is in communication with both the hand piece and the pair of jaws. The first constraint comprises a first slot and a mating first pin. The first slot is on the actuator and the first pin is on one or both of the first jaw and the second jaw, or the first pin is on the actuator and the first slot is on one or both of the first jaw and the second jaw. The second constraint comprises a second slot and a mating second pin. The second slot is on the actuator and the second pin is on one or both of the first jaw and the second jaw, or the second pin is on the actuator and the second slot is on one or both of the first jaw and the second jaw. The third constraint restrains movement of the pair of jaws relative to the introducer. Movement of the actuator causes the pair of jaws to move between an open configuration and a closed configuration. During movement from the open configuration to the closed configuration, the pair of jaws undergo a translational movement relative to the introducer or hand piece followed by a first non-translational movement relative to the introducer or handpiece.

Further yet, these teachings provide an instrument, comprising a hand piece; an introducer; a pair of jaws; an actuator; a first constraint; a second constraint; and a third constraint. The introducer extends from the hand piece. The pair of jaws extend form the introducer. The pair of jaws comprise a first jaw including a first jaw armature and a first gripping surface and a second jaw. The actuator is in communication with both the hand piece and the pair of jaws. The first constraint comprises a first slot and a mating first pin. The first slot is on the actuator and the first pin is on the first jaw armature, or the first pin is on the actuator and the first slot is on the first jaw armature. The second constraint comprises a second slot and a mating second pin. The second slot is on the actuator and the second pin is on the first jaw armature, or the second pin is on the actuator and the second slot is on the first jaw armature. The third constraint restraints movement of the pair of jaws relative to the introducer.

Still further yet, these teachings further provide an instrument, comprising a hand piece; an introducer, a pair of jaws; an actuator, a first constraint; a second constraint; and a third constraint. The introducer extends from the hand piece. The pair of jaws extend form the introducer. The pair of jaws comprise a first jaw and a second jaw. The actuator is in communication with both the hand piece and the pair of jaws. The first constraint comprises a first slot and a mating first pin. The second constraint comprises a second slot and a mating second pin. Both the first slot and the second slot are on the actuator and both the first pin and the second pin are on one or both of the first jaw and the second jaw. Or, both the first slot and the second slot are on one or both of the first jaw and the second jaw and both the first pin and the second pin are on the actuator. The third constraint comprises a link that is pivotally connected at one end to the introducer and at the other end to one or both of the first jaw and the second jaw.

These teachings provide an instrument, comprising a hand piece; an introducer a pair of jaws; an actuator, a first constraint; a second constraint; and a third constraint. The introducer extends from the hand piece. The pair of jaws extend form the introducer. The pair of jaws comprise a first jaw and a second jaw. The actuator is in communication with both the hand piece and the pair of jaws. The first constraint comprises a first slot and a mating first pin. The first slot is on the introducer and the first pin is on one or both of the first jaw and the second jaw, or the first pin is on the introducer and the first slot is on one or both of the first jaw and the second jaw. The second constraint comprises a second slot and a mating second pin. The second slot is on the introducer and the second pin is on one or both of the first jaw and the second jaw, or the second pin is on the introducer and the second slot is on one or both of the first jaw and the second jaw. The third constraint comprising a third slot and a mating third pin. The third slot is on the actuator and the third pin is on is one or both of the first jaw and the second jaw, or the third pin is on the actuator and the third slot is on is one or both of the first jaw and the second jaw.

These teachings provide an instrument, comprising a hand piece; an introducer; a pair of jaws; an actuator; a first constraint; a second constraint; and a third constraint. The introducer extends from the hand piece. The pair of jaws extend form the introducer. The pair of jaws comprise a first jaw including a first jaw armature and a first gripping section, and a second jaw. The actuator is in communication with both the hand piece and the pair of jaws. The first constraint comprises a first slot and a mating first pin. The first slot is on the introducer and the first pin is on the first jaw armature, or the first pin is on the introducer and the first slot is on the first jaw armature. The second slot is on the introducer and the first pin is on the first jaw armature, or the second pin is on the introducer and the second slot is on the first jaw armature. The third slot is on the actuator and the third pin is on the first jaw armature, or the third pin is on the actuator and the third slot is on the first jaw armature. The third constraint restrains movement of the first jaw armature relative to the actuator These teachings also provide an instrument comprising a hand piece; a pair of jaws extending from the hand piece; and an actuator in communication with both the hand piece and the pair of jaws. Each of the jaws include gripping surface, which comprises a proximal portion and a distal portion. Movement of the actuator causes the pair of jaws to move from an open configuration to a closed configuration. During the move from the open configuration to the closed configuration, the pair of jaws undergo a first closing movement followed by a second closing movement. During the first closing movement, the distal portion of one of the jaws moves along an axis that is generally perpendicular to the gripping surface of the other jaw. During the second closing movement, the distal portion of one of the jaws moves along another axis relative to the gripping surface of the other jaw.

An instrument comprising a hand piece; a pair of jaws extending from the hand piece, each of the jaws include a proximal portion and a distal portion; and an actuator in communication with both the hand piece and the pair of jaws. Movement of the actuator causes the pair of jaws to move between an open configuration and a closed configuration. During the move from the open configuration to the closed configuration, the pair of jaws undergo a translational movement relative to one another followed by a first non-translational movement relative to one another.

Each of the pair of jaws comprise a gripping surface, and during the translational movement, the gripping surfaces remain generally parallel relative to one another.

The pair of jaws comprise a first jaw and a second jaw, and during the translational movement, the distal portion of the first jaw is moved towards the gripping surface of the second jaw along an axis that is generally perpendicular to the gripping surface of the second jaw, and after the translational movement, the pair of jaws undergo the first non-translational movement where the distal portion of the first jaw is moved towards the gripping surface of the second jaw while simultaneously also being moved proximally relative to the distal portion of the second jaw.

During the first non-translational movement, a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaws are moved such the gap defined between the proximal portions is taken up.

During the first non-translational movement, one or both of the pair of jaws are moved such that a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaw are moved such that the gap defined between the proximal portions is taken up.

An instrument, comprising: a hand piece; a pair of jaws extending from the hand piece, each of the jaws include a proximal portion and a distal portion; and an actuator in communication with both the hand piece and the pair of jaws. Movement of the actuator affects a translational movement of the pair of jaws and a first non-translational movement of the pair of jaws. The first non-translational movement occurs when the pair of jaws are closer together than when the pair of jaws are undergoing the translational movement.

Each of the pair of jaws comprise a gripping face, and during the translational movement, the gripping faces remain generally parallel relative to one another.

The pair of jaws comprises a first jaw and a second jaw, and during the translational movement, the distal portion of the first jaw is moved towards the gripping surface of the second jaw along an axis that is generally perpendicular to the gripping surface of the second jaw, and after the translational movement, the pair of jaws undergo the first non-translational movement where the distal portion of the first jaw is moved towards the gripping surface of the second jaw while simultaneously also being moved proximally relative to the distal portion of the second jaw.

At the end of the first non-translational movement, the distal portions are closer together than the proximal portions, and the first non-translational movement is followed by a second-non-translational movement where one or both of the pair of jaws are moved such the proximal portions are closer together than the distal portions.

At the end of the first non-translational movement the distal portions are in contact with one another while a gap is defined between the proximal portions, and the first non-translational movement is followed by a second-non-translational movement where one or both of the pair of jaws are moved such the gap defined between the proximal portions is taken up.

During the first non-translational movement, one or both of the pair of jaws are moved such that a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

An instrument comprising: a hand piece; an introducer extending from the hand piece; a pair of jaws extending form the introducer, the pair of jaws comprising: a first jaw; and a second jaw; an actuator in communication with both the hand piece and the pair of jaws; and a first constraint comprising a first slot and a mating first pin. The first slot is on the actuator and the first pin is on one or both of the first jaw and the second jaw, or the first pin is on the actuator and the first slot is on one or both of the first jaw and the second jaw. A second constraint comprising a second slot and a mating second pin. The second slot is on the actuator and the second pin is on one or both of the first jaw and the second jaw, or the second pin is on the actuator and the second slot is on one or both of the first jaw and the second jaw. A third constraint that restrains movement of the pair of jaws relative to the introducer. Movement of the actuator causes the pair of jaws to move between an open configuration and a closed configuration. During movement from the open configuration to the closed configuration, the pair of jaws undergo a translational movement followed by a first non-translational movement.

The third constraint comprises a third slot and a mating third pin, and the third slot is on the actuator and the third pin is on one or both of the first jaw and the second jaw, or the third pin is on the actuator and the third slot is on one or both of the first jaw and the second jaw.

The third constraint comprises a link that is pivotally connected at one end to the introducer and at the other end to one or both of the first jaw and the second jaw.

Each of the pair of jaws comprise a gripping surface, and during the translational movement, the gripping surfaces remain generally parallel relative to one another.

The pair of jaws comprises a first jaw and a second jaw, each of the first jaw and the second jaw have a distal portion and a proximal portion, and during the translational movement, the distal portion of the first jaw is moved towards the gripping surface of the second jaw along an axis that is generally perpendicular to the gripping surface of the second jaw, and after the translational movement, the pair of jaws undergo the first non-translational movement where the distal portion of the first jaw is moved towards the gripping surface of the second jaw while simultaneously also being moved proximally relative to the distal portion of the second jaw.

During the first non-translational movement, a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaws are moved such the gap defined between the proximal portions is taken up.

During the first non-translational movement, one or both of the pair of jaws are moved such that a gap defined between opposing distal portions of the pair of jaws closes faster than a gap defined between opposing proximal portions of the pair of jaws, and the first non-translational movement is followed by a second-non-translational movement where one or both of the pair of jaw are moved such that the gap defined between the proximal portions closes faster than the gap defined between the distal portions.

At the end of the first non-translational movement, opposing distal portions of the pair of jaws are in contact with one another while a gap is defined between opposing proximal portions of the pair of jaws, and the first non-translational movement is followed by a second-non-translational movement where one or both of the pair of jaw are moved such that the gap defined between the proximal portions is taken up.

An instrument, comprising: a hand piece; an introducer extending from the hand piece; a pair of jaws extending from the introducer, the pair of jaws comprising: a first jaw including a first jaw armature and a first gripping surface; and a second jaw; an actuator in communication with the hand piece and the pair of jaws; a first constraint comprising a first slot and a mating first pin. The first slot is on the actuator and the first pin is on the first jaw armature, or the first pin is on the actuator and the first slot is on the first jaw armature. A second constraint comprising a second slot and a mating second pin. The second slot is on the actuator and the second pin is on the first jaw armature, or the second pin is on the actuator and the second slot is on the first jaw armature. A third constraint that restraints movement of the pair of jaws relative to the introducer.

The third constraint comprises a third slot and a mating third pin, and the third slot is on the introducer and the third pin is on the first jaw armature, or the third pin is on the introducer and the third slot is on the first jaw armature.

The third constraint comprises a link that is pivotally connected at one end to the introducer and at the other end to the first jaw armature.

The second jaw includes a second jaw armature and a second jaw member, and the first slot is on the actuator and the first pin is on the first jaw armature and the second jaw armature, or the first pin is on the actuator and the first slot is on the first jaw armature and the second jaw armature, and the second slot is on the actuator and the second pin is on the first jaw armature and the second jaw armature, or the second pin is on the actuator and the second slot is on the first jaw armature and the second jaw armature.

Movement of the actuator causes the first jaw armature and the second jaw armature move between an open configuration and a closed configuration, and during movement from the open configuration to the closed configuration, the first jaw armature and the second jaw armature undergo a translational movement relative to each other followed by a first non-translational movement relative to each other.

The third constraint comprises a third slot and a mating third pin, and the third slot is on the actuator and the third pin is on one or both of the first jaw and the second jaw, or the third pin is on the actuator and the third slot is on one or both of the first jaw and the second jaw.

The third constraint comprises a link that is pivotally connected at one end to the introducer and at the other end to one or both of the first jaw and the second jaw.

During the translational movement, the first jaw armature and the second jaw armature remain generally parallel relative to one another.

During the translational movement, the distal portion of the first armature is moved towards the second jaw armature along an axis that is generally perpendicular to the second jaw armature, and after the translational movement, the pair of jaws undergo the first non-translational movement where the distal portion of the first jaw armature is moved towards the second jaw armature while simultaneously also being moved proximally relative to the distal portion of the second jaw armature.

During the first non-translational movement, a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaws are moved such the gap defined between the proximal portions is taken up.

An instrument, comprising: a hand piece; an introducer extending from the hand piece; a pair of jaws extending form the introducer, the pair of jaws comprising a first jaw and a second jaw; an actuator in communication with both the hand piece and the pair of jaws; a first constraint comprising a first slot and a mating first pin; a second constraint comprising a second slot and a mating second pin. Both the first slot and the second slot are on the actuator and both the first pin and the second pin are on one or both of the first jaw and the second jaw, or both the first slot and the second slot are on one or both of the first jaw and the second jaw and both the first pin and the second pin are on the actuator. A third constraint comprising a link that is pivotally connected at one end to the introducer and at the other end to one or both of the first jaw and the second jaw.

The first jaw includes a first jaw armature and a first jaw member, and both the first slot and the second slot are on the actuator and both the first pin and the second pin are on the first jaw armature, or both the first slot and the second slot are on the first jaw armature and both the first pin and the second pin are on the actuator.

The second jaw includes a second jaw armature and a second jaw member, and both the first slot and the second slot are on the actuator and both the first pin and the second pin are on one or both of the first jaw armature and the second jaw armature, or both the first slot and the second slot are on one or both of the first jaw armature and the second jaw armature and the second jaw and both the first pin and the second pin are on the actuator.

The link that is pivotally connected at one end to the introducer and at another end to the first jaw armature.

The link that is pivotally connected at one end to the introducer and at the other end to one or both of the first jaw armature and the second jaw armature.

Movement of the actuator causes the pair of jaws to move between an open configuration and a closed configuration, and during movement from the open configuration to the closed configuration, the pair of jaws undergo a translational movement followed by a first non-translational movement.

Each of the pair of jaws comprise a gripping surface, and during the translational movement, the gripping surfaces remain generally parallel relative to one another.

The pair of jaws comprises a first jaw and a second jaw, and during the translational movement, the distal portion of the first jaw is moved towards the gripping surface of the second jaw along an axis that is generally perpendicular to the gripping surface of the second jaw, and after the translational movement, the pair of jaws undergo the first non-translational movement where the distal portion of the first jaw is moved towards the gripping surface of the second jaw while simultaneously also being moved proximally relative to the distal portion of the second jaw.

During the first non-translational movement, a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaws are moved such the gap defined between the proximal portions is taken up.

During the first non-translational movement, one or both of the pair of jaws are moved such that a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaw are moved such that the gap defined between the proximal portions is taken up.

An instrument, comprising: a hand piece; an introducer extending from the hand piece; a pair of jaws extending form the introducer, the pair of jaws comprising a first jaw and a second jaw; an actuator in communication with both the hand piece and the pair of jaws; a first constraint comprising a first slot and a mating first pin. The first slot is on the introducer and the first pin is on one or both of the first jaw and the second jaw, or the first pin is on the introducer and the first slot is on one or both of the first jaw and the second jaw. A second constraint comprising a second slot and a mating second pin. The second slot is on the introducer and the second pin is on one or both of the first jaw and the second jaw, or the second pin is on the introducer and the second slot is on one or both of the first jaw and the second jaw. A third constraint comprising a third slot and a mating third pin. The third slot is on the actuator and the third pin is on is one or both of the first jaw and the second jaw, or the third pin is on the actuator and the third slot is on is one or both of the first jaw and the second jaw.

Movement of the actuator causes the pair of jaws to move between an open configuration and a closed configuration, during movement from the open configuration to the closed configuration, the pair of jaws undergo a translational movement over a first range of motion followed by a first non-translational movement over a second range of motion, during the translational movement, one or both of the jaws are moved towards one another while remaining generally parallel relative to one another, and during the first non-translational movement, one or both of the jaws are moved angularly towards one another.

Movement of the actuator causes the pair of jaws to move between an open configuration and a closed configuration, and during the movement from the open configuration to the closed configuration, the pair of jaws undergo a translational movement followed by a first non-translational movement.

Each of the pair of jaws comprise a gripping surface, and during the translational movement, the gripping surfaces remain generally parallel relative to one another.

The pair of jaws comprises a first jaw and a second jaw, and during the translational movement, the distal portion of the first jaw is moved towards the gripping surface of the second jaw along an axis that is generally perpendicular to the gripping surface of the second jaw, and after the translational movement, the pair of jaws undergo the first non-translational movement where the distal portion of the first jaw is moved towards the gripping surface of the second jaw while simultaneously also being moved proximally relative to the distal portion of the second jaw.

During the first non-translational movement, a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement, the distal portions are in contact with one another while a gap is defined between the proximal portions, and the first non-translational movement is followed by a second-non-translational movement where one or both of the pair of jaws are moved such the gap defined between the proximal portions is taken up.

During the first non-translational movement, one or both of the pair of jaws are moved such that a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaw are moved such that the gap defined between the proximal portions is taken up.

An instrument, comprising: a hand piece; an introducer extending from the hand piece; a pair of jaws extending from the introducer, the pair of jaws comprising: a first jaw including a first jaw armature and a first gripping section; and a second jaw; an actuator in communication with both the hand piece and the pair of jaws; a first constraint comprising a first slot and a mating first pin. The first slot is on the introducer and the first pin is on the first jaw armature, or the first pin is on the introducer and the first slot is on the first jaw armature. A second constraint comprising a second slot and a mating second pin. The second slot is on the introducer and the first pin is on the first jaw armature, or the second pin is on the introducer and the second slot is on the first jaw armature. A third constraint comprising a third slot and a mating third pin. The third slot is on the actuator and the third pin is on the first jaw armature, or the third pin is on the actuator and the third slot is on the first jaw armature, and the third constraint restrains movement of the first jaw armature relative to the actuator.

The second jaw includes a second jaw armature and a second jaw member, the first slot is on the introducer and the first pin is on both of the first jaw armature and the second jaw armature, or the first pin is on the introducer and the first slot is on both the first jaw armature and the second jaw armature, and the second slot is on the introducer and the second pin is on both of the first jaw armature and the second jaw armature, or the second pin is on the introducer and the second slot is on both the first jaw armature and the second jaw armature.

Movement of the actuator causes the pair of jaws to move between an open configuration and a closed configuration, and during the movement from the open configuration to the closed configuration, the pair of jaws undergo a translational movement followed by a first non-translational movement.

Each of the pair of jaws comprise a gripping surface, and during the translational movement, the gripping surfaces remain generally parallel relative to one another.

The pair of jaws comprises a first jaw and a second jaw, and during the translational movement, the distal portion of the first jaw is moved towards the gripping surface of the second jaw along an axis that is generally perpendicular to the gripping surface of the second jaw, and after the translational movement, the pair of jaws undergo the first non-translational movement where the distal portion of the first jaw is moved towards the gripping surface of the second jaw while simultaneously also being moved proximally relative to the distal portion of the second jaw.

During the first non-translational movement, a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaws are moved such the gap defined between the proximal portions is taken up.

During the first non-translational movement, one or both of the pair of jaws are moved such that a gap defined between the distal portions closes faster than a gap defined between the proximal portions, and the first non-translational movement is followed by a second-non-translational movement where one or both of the pair of jaw are moved such that the gap defined between the proximal portions closes faster than the gap defined between the distal portions.

At the end of the first non-translational movement the distal portions are in contact with one another while a gap is defined between the proximal portions, and the first non-translational movement is followed by a second-non-translational movement where one or both of the pair of jaw are moved such that the gap defined between the proximal portions is taken up.

An instrument, comprising: a hand piece; a pair of jaws extending from the hand piece, each of the jaws include gripping surface, which comprises a proximal portion and a distal tip; and an actuator in communication with both the hand piece and the pair of jaws. Movement of the actuator causes the pair of jaws to move from an open configuration to a closed configuration. During the movement from the open configuration to the closed configuration, the pair of jaws undergo a first movement followed by a second movement. During the first movement, the distal tip of one of the jaws moves along a path that is generally perpendicular to the gripping surface of the other jaw and the path is free of a movement component along a path that is generally parallel to the gripping surface. During the second movement, the distal tip of one of the jaws moves along a path relative to the gripping surface of the other jaw that includes a movement component that is generally parallel to the gripping surface of the other jaw.

The second movement comprises a translational movement where the gripping surfaces of the pair of jaws remain substantially parallel relative to one another.

The second movement is a non-translational movement where the gripping surfaces of the pair of jaws are in a non-parallel relationship relative to one another.

During the second movement, a gap defined between the distal tips closes faster than a gap defined between the proximal portions, and the distal tip of one of the jaws moves proximally relative to the distal tip of the other jaw.

DETAILED DESCRIPTION

Figure 1:
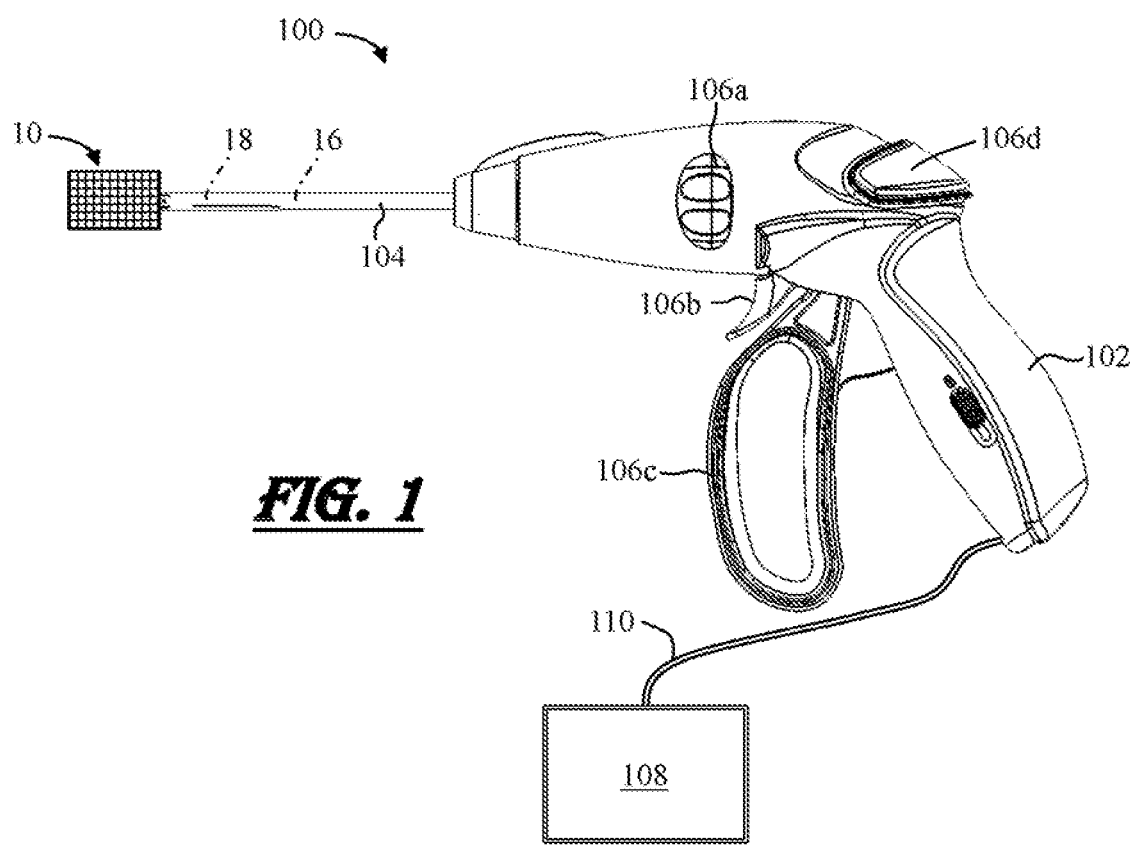
FIG. 1 is a side view of an instrument having a jaw assembly of any of the jaw assemblies shown and/or described herein.

This disclosure claims the benefit of U.S. 62/471,087 filed on Mar. 14, 2017, which is entirely incorporated by reference herein for all purposes.

These teachings provide an instrument. The instrument may be a medical instrument or a non-medical instrument. The instrument may be forceps. The instrument can be virtually any forceps known in the field. For example, the forceps may be medical forceps, cutting forceps, electrosurgical forceps, bipolar forceps, the like, or a combination thereof.

The instrument may be any instrument or device for effecting an object or anatomical feature. Effecting may mean, for example, holding, manipulating, engaging, moving, grasping, gripping, constricting, pushing, pulling, cutting, tearing, coagulating, sealing, cauterizing, dissecting, fulgurating, or a combination thereof an object or anatomical feature. The anatomical feature may be any anatomical feature, such as a vessel, tissue, vein, artery, the like, or a combination thereof. The instrument can be used in virtually any procedure: medically related or otherwise. In medical procedures, the instrument can be used in open procedures, laparoscopic procedures, or both. The instrument may be any instrument or device having arms and/or jaws.

The instrument can be used with or without power. When used with power, one or more electrical currents, therapies, and/or signals may be provided to the instrument to electrically affect an object or anatomical feature. The power, one or more electrical currents, therapies, and/or signals may be provided via a generator or other suitable power source. The power source may be of the type described in U.S. Pat. No. 7,282,048B2, the teachings of which are hereby incorporated by reference herein for all purposes. The one or more electrical currents, therapies, and/or signals may be provided to, through, and/or between the jaw assembly, the one or more jaws, the blade, one or more electrodes, a remote pad or electrode, or a combination thereof.

The one or more electrical currents, therapies, and/or signals provided by the power source may be monopolar energy, bipolar energy, blended energy, or a combination thereof. The one or more electrical currents, therapies, and/or signals may include a cut waveform, a coagulation waveform, and/or a blended waveform. During use, an electrical circuit may be completed by passing monopolar energy from the power source to the one or more jaws, blades, and/or electrodes, to the object or anatomical feature of interest, and to a remote pad or electrode. During use, an electrical circuit may be completed by passing bipolar energy from the power source to an active electrode or active feature of the one or more jaws, blade, and/or electrodes, through the object or anatomical feature of interest, and to a return electrode or portion of jaws, arms, or a combination thereof. The cut waveform may be delivered continuously from the power source to the blade or instrument, and can be described as a higher current/lower voltage waveform compared to the coagulation waveform. The coagulation waveform may be modulated or interrupted from the power source to the instrument, and can be described as a lower current/higher voltage waveform compared to the cut waveform. The blended waveform may be a combination of a cut waveform and a coagulation waveform. The blended waveform may advantageously allow a user to coagulate the object or anatomical feature while also cutting the object or anatomical feature. The blended waveform may be of the type described in the above-mentioned U.S. Pat. No. 7,282,048B2, which has been incorporated by reference herein for all purposes.

The instrument may include a hand piece. The hand piece may function to house, support, and/or contain the introducer, the actuator, the jaws, the blade, or a combination thereof. The hand piece may function to house, support, and/or contain the parts, components and/or mechanism required for operating, actuating, moving, reciprocating, opening, closing, retracting, extending, rotating, and/or manipulating the introducer, the actuator, the one or more jaws, blades, or a combination thereof.

The hand piece may include sufficient controls for operating, actuating, moving, reciprocating, opening, closing, retracting, extending, rotating, and/or manipulating the introducer, the actuator, the one or more jaws, blades, or a combination thereof. The one or more user controls may include one or more triggers, wheels, levers, buttons, knobs, the like, or a combination thereof. For example, the wheel may be adapted to be moved or manipulated to rotate the jaw assembly about a longitudinal axis of the jaw assembly, the introducer, or both. For example, the trigger may be adapted to be moved or manipulated so that the blade is translated or reciprocated about the longitudinal axis of the cut blade, the introducer, the jaw assembly, or a combination thereof. For example, the button may be adapted to be moved or manipulated so that a therapeutic current or signal from the power supply is applied to the jaw assembly, one or both of the jaws, the gripping portion, one or more electrically conductive sections, one or more of the electrodes, a remote pad, a patient or anatomy, or a combination thereof so that an object or anatomical feature can electrically effected. For example, the lever may be adapted to be moved towards the handle so that the actuator is moved proximally or distally relative to the introducer so that the jaw assembly moves from the closed configuration towards the open configuration or from the open configuration towards the closed configuration.

The instrument may include an introducer. The introducer may function to permit a portion of the instrument to be inserted into a patient or the anatomy, while a portion of the instrument remains outside of the patient or anatomy. The introducer may be configured to be inserted into the anatomy through a trocar. The introducer may allow for the jaw assembly and/or one or more functional elements of the instrument, such as the actuator or blade, to be manipulated without being impeded by a trocar, the anatomy, or both.

The introducer may be an elongated, tubular member or structure that extends along a longitudinal axis. The introducer may be a tube. The proximal end of the introducer may be fixedly connected to the hand piece so that the introducer is prevented or restricted from being moved or translated independently of the hand piece. The introducer may be substantially straight; may include one or more angles, bends or arcs; or a combination thereof. The introducer may be substantially rigid, substantially bendable flexible, substantially resilient, or a combination thereof.

The introducer may be at least partially hollow and may define therein an inner portion or inner space. The hollow or inner portion or space of the introducer may be sufficiently sized so that one or more jaws, a jaw assembly, a cut blade, an inner member, or a combination thereof can be received in the outer member. The inner member may be received in the outer member such that the two members share a common longitudinal axis. Alternatively, a center longitudinal axis of the inner member may be offset or spaced apart from a center longitudinal axis of the outer member. Offset may mean that the center longitudinal axis of the inner member is spaced apart or generally coplanar with a center longitudinal axis of the outer member in a vertical direction or along a vertical axis; in a lateral or transverse direction or along a lateral or transverse axis; or in a direction or along an axis therebetween.

The instrument may include a jaw assembly. The jaw assembly may function to effect an object or anatomical feature. For example, the jaw assembly, or the one or more jaws that comprise the jaw assembly, may be used to hold, capture, grip, grasp, manipulate, compress, secure, retract, engage, move, push, pull, cut, tear, coagulate, seal, cauterize, dissect, fulgurate, or a combination thereof an object or anatomical feature. For example, the jaw assembly, or the one or more jaws that comprise the jaw assembly, may be used in electrosurgery to electrically cut, coagulate, cauterize, dissect, and/or fulgurate an object anatomical feature. The anatomical feature may be, for example, a vessel, tissue, vein, artery, a portion of the anatomy, or a combination thereof. The jaw assembly, or the one or more jaws that comprise the jaw assembly, may function to effect an object or anatomical feature when the jaw assembly is in an open configuration, a closed configuration, or in a position or configuration therebetween.

The instrument may include one or more jaws. The jaw assembly may include one or more jaws. One or more of the jaws may be moved, adjusted, manipulated, repositioned, opened, closed, rotated, and/or adapted to perform one or more effecting functions. The jaws may oppose one another. The jaws may include a first or upper jaw and an identical second or lower jaw. Alternatively, the opposing jaws need not be identical. In other words, the geometry of the upper jaw may be different from the lower jaw. The jaws may be substantially rigid; substantially flexible; substantially resilient, or a combination thereof. That is, the jaws may have one or more sections or portions that are substantially rigid; one or more sections or portions that are substantially flexible; one or more sections or portions that are substantially resilient, or a combination thereof.

The jaws may be fabricated from any suitable material. Preferably, the jaws are fabricated from a material that is suitable for use in medical procedures, and is rigid. For example, the jaw elements may be made from sheet metal or wire. The jaws may be formed by any suitable process, such as stamping, metal injection molding (MIM), or plastic injection molding, for example. The jaws may be fabricated from a material that can pass current so that one or more of the jaws can be used in electrosurgery. One or both of the jaws, or portions thereof, may be electrically conductive. One or both jaws, or portions thereof, may be non-electrically conductive. The jaws may be thermally insulating so that a thermal barrier can be provided between the jaws, the jaw assembly, or both. A thermally insulating jaw may be preferred in some applications so that thermal spread is limited or reduced. One or more sections of the jaws may be covered or coated in an insulating material so that electrical shorts can be prevented if the jaws come into contact with one another.

The jaws may comprise a gripping surface. The gripping surface may be at least partially smooth, flat, contoured, serrated, textured, horizontal, vertical, planar, canted, rolling, or a combination thereof. The gripping surface may include one or more areas having teeth, no teeth, or both. The one or more teeth may be formed or cut into the jaw or gripping surface by a suitable process or method, such as by grindinding, electrical discharge machining, stamping, coining, etc. The one or more teeth may have sharp points to assist in grasping an object or anatomical feature. Alternatively, or in addition, the one or more teeth may have flattened tops to distribute forces associated with grasping forces so that the object or tissue, especially vessel walls, are not punctured or otherwise damaged when an object, vessel, or tissue is between the jaws in the closed configuration.

The gripping surface may be electrically conductive. That is, the gripping surface may include one or more electrically conductive sections. An electrically conductive section may function to pass one or more therapy signals or currents between the gripping surface, electrically conductive section, an object, the anatomy, or a combination thereof. The electrically conductive section may be, or may include, an electrode that is in communication with a power source. The electrically conductive may be an entire portion of the gripping surface. The electrically conductive sections may comprise a smaller area or section than the entire gripping surface.

The gripping surface may include one or more insulated sections or non-electrically conductive sections. The one or more insulated or non-electrically conductive sections may be insulated or otherwise not connected to an electrode or power source. Accordingly, the one or more non-electrically conductive sections may be unable or restricted from passing a therapy current between the jaws, an object, the anatomy, or a combination thereof. An insulated section or non-electrically conductive section may function to prevent an electrically charged blade from contacting the jaws. The gripping surface and/or the one or more jaws may include an insulator to prevent one or more electrically charged jaws from contacting the blade.

The jaw assembly and/or one or more jaws may be moved between an open configuration and a closed configuration.

The one or more jaws may include an armature. The armature may function to provide for the jaw or a jaw portion to pivot or move relative to the armature. The armature may function to provide for an equal or substantially equal gripping force between the proximal and distal portions of a jaw, a jaw portion, a gripping surface, or a combination thereof. The first jaw may include an armature, the second jaw may include an armature, or both jaws may include an armature.

The instrument may include one or more actuators. The actuator may be in communication with the hand piece and/or one or more controls on the hand piece so that the actuator can be moved may manipulating, moving, or otherwise actuating one or more controls on the hand piece. Movement of the actuator may mean that the actuator is moved distally relative to a stationary hand piece, proximally relative to a stationary hand piece, rotationally, or a combination thereof. The actuator may be moved along a longitudinal axis of the actuator or introducer.

Movement of the actuator may function to move one or both of the jaws. For example, movement or actuation of one or more controls on the hand piece may function to move or actuate the actuator, which may cause one or both of the jaws to move, open, close, retract, flex, bend, extend, articulate, rotate, or a combination thereof. Movement of the actuator may function to move one or both of the jaws between an open configuration and a closed configuration. That is, when moving between an open configuration and a closed configuration (or vice versa), the actuator may function to move a first jaw relative to a static second jaw; move a second jaw relative to a static first jaw; or move both jaws relative to one another. Movement of the actuator may affect a translational movement of one or both of the jaws and/or affect more non-translational movements of one or both of the jaws.

The actuator may be an elongated member or beam that is received in the introducer. The inner member may be coaxial to the outer tube. The actuator may be a shaft. The actuator may be a shaft or rod that is solid in cross section. The actuator may have a circular cross section, or the actuator may have a rectangular cross section. The actuator may be a tube that is hollow. The actuator may be a rod, a strap, a mechanism, the introducer, one or more supports, or a combination thereof. The actuator may function to move the blade (e.g., extend, retract, rotate, reciprocate, or a combination thereof). The actuator that moves the blade may be the same actuator that moves one or both of the jaws, or may be a different actuator, rod, or mechanism.

The instrument may include one or more constraints. The one or more constraints may function to connect the actuator to one or both of the jaws. The one or more constraints may function to move one or both of the jaws relative to the hand piece, the introducer, relative to each other, relative to the anatomy, a user, a site of interest, or a combination thereof. The one or more constraints may function to restrain movement of one or both of the jaws relative to the hand piece, the introducer, relative to each other, relative to the anatomy, a user, a site of interest, or a combination thereof.

The one or more constraints may be any device that may perform one or more of the aforementioned functions. For example, the one or more constraints may comprise one or more pins, slots, apertures, or a combination thereof. One or more pins may be located on a respective jaw and one or more mating slots or apertures may be located on the actuator or introducer, or vice versa. For example, a first pin may be located on one or both of the jaws, and a mating first slot or aperture may be located on the actuator or introducer, or vice versa. For example, a second pin may be located on one or both of the jaws, and a mating second slot or aperture may be located on the actuator or introducer, or vice versa. For example, a third pin may be located on one or both of the jaws, and a mating third slot or aperture may be located on the actuator or introducer, or vice versa. In other words, any number of pins may be located on one or both of the jaws and any number of mating slots or apertures may be located on the actuator, or vice versa.

The instrument may include one or more links. The one or more links may restrain movement of one or more of the jaws and/or armatures relative to one another, relative to the body, the introducer, or point of reference. The one or more links may be one or more constraints. The link can be pivotally connected at one end to the introducer or the actuator and at the other end to one or more jaws.

The instrument may include one or more slots. The one or more slots may extend generally vertical or generally perpendicular relative to a gripping surface or reference point, generally parallel relative to a gripping surface or reference point; generally angularly relative to a gripping surface or reference point, or a combination thereof. The one or more slots may have an "L" shape. The one or more slots may be elongated so that a mating pin can translate through the slot. The one or more slots may be substantially circular and may correspond generally to the shape of a mating pin so that the pin rotates therein without translating. The one or more slots may have any suitable geometry in order to achieve one or more of the jaw translational and/or non-translational movements described herein.

The jaw assembly and/or one or more jaws may be moved between an open configuration and a closed configuration.

The open position may be a steady state position, and the jaw assembly may be moved from the open configuration to the closed configuration by manipulating one or more user controls on the hand piece, such as the lever. In the open configuration, the one or more jaws and/or gripping surfaces may be in a spaced apart relationship relative to one another. In the open configuration, a gap defined between the opposing proximal portions of the opposing jaws and/or gripping surfaces may be larger, smaller, or the same size as a gap defined between the opposing distal portions of the opposing jaws and/or gripping surfaces. In the open configuration, the opposing jaws and/or gripping surfaces may be further spaced apart relative to one another than when the jaw assembly is in the closed or gripping configuration.

The closed or gripping configuration may be defined as a position of the jaws or the jaw assembly where virtually no gap, or only a slight gap, exists between the jaws or gripping surfaces. In the closed configuration, a clamping or gripping force of the gripping surfaces may be higher or larger than a clamping or gripping force between the gripping surfaces when the jaws are in the open configuration. In the closed configuration, the distal portions of the opposing jaws and/or gripping surfaces may be in contact with each other, while the proximal portions are in a spaced apart relationship relative to one another, or vice versa. In the closed configuration, a gap defined between the opposing proximal portions of the jaws and/or gripping surfaces may be larger, smaller, or the same size as a gap defined between the opposing distal portions. In the closed or gripping configuration, the opposing jaws and/or gripping surfaces may be less spaced apart relative to one another than in the open configuration.

When moving between the open configuration and the closed position and/or the closed configuration and the open configuration, the one or more jaws may undergo one or more movements. In other words, it is understood that any of the movements described herein can be performed in virtually any order when the jaw assembly is moved between the open configuration and the closed or gripping configuration, or vice versa.

When moving between the open configuration and the closed or gripping configuration, or the closed configuration and the open configuration, the jaws may undergo one or more translational movements, one or more non-translational movements, or both. The or more translational movement may be preceded by, or followed by, one or more non-translational movements.

During any of the movements described herein, jaws, armatures, actuator, gripping surfaces, or a combination there of may be moved relative to a reference point. The reference point may include, for example, one or more of: an opposing jaw, armature, gripping surface, or a combination thereof; a site of interest; the anatomy; the introducer; the hand piece; an operator, the ground or floor; one or more of the proximal portions; one or more of the distal portions; or a combination thereof.

A translational movement may refer to any one or more of the movements described herein, including any of the non-translational movements. A translational movement may refer to a movement where the jaws, gripping surfaces, armatures, or a combination thereof are maintained in a generally parallel relationship relative to one another.

A translational movement may occur when the opposing jaws, gripping surfaces, armatures, or a combination thereof are closer together than during a non-translational movement. Alternatively, a translational movement may occur when the opposing jaws, gripping surfaces, armatures, or a combination thereof are farther apart than during a non-translational movement.

During a translational movement, the jaws, armatures, and/or gripping surfaces may be maintained in a generally parallel relationship relative to one another while one of the jaws, gripping surfaces, and/or armatures is moved towards or away from the opposing jaw, gripping surface, and/or armature. Alternatively, during a translational movement, the armatures, jaws, and/or gripping surfaces may be maintained in a generally parallel relationship relative to one another while both of the opposing armatures, jaws, and/or gripping surfaces are moved towards or away from one another.

During a translational movement, one or both of the armatures may be maintained parallel to one another or moved parallel to one another while the opposing jaws and/or gripping surfaces are not maintained in parallel or not moved in parallel relative to one another.

During a translational movement, one or both of the armatures, jaws, and/or gripping surfaces may be moved towards or away from one another in a manner such that a difference or magnitude in the gap defined between the opposing proximal portions and the opposing distal portions or tips of the jaws and/or gripping surfaces remains substantially the same.

During a translational movement, a distal portion or tip of one of the jaws or gripping surfaces may move towards or away from the opposing jaw or griping surface along an axis that is generally perpendicular to the opposing jaw, or gripping surface.

During a translational movement, one or both of the armatures, jaws, and/or gripping surfaces may be moved axially (e.g., distally, proximally, or both) relative to the introducer, the hand piece, or any other reference point. During a translational movement, one or both of the arms, armatures, jaws, and/or gripping surfaces may not move axially (e.g., distally, proximally, or both) relative to the introducer, the hand piece, or any reference point.

During a translational movement, a distal portion or tip of one of the jaws or gripping surfaces may move along a path that is generally perpendicular to the opposing gripping surface. The path may be free of any movements or movement components along a path that is generally parallel to the gripping surface. In other words, the path may be free of a horizontal movement or component relative to the introducer, hand piece, and/or point of reference.

During a translational movement, a distal portion or tip of one of the jaws or gripping surfaces may move along a path that is generally parallel to the gripping surface of the opposing griping surface. The path may be free of any movements or movement components along a path that is generally perpendicular to the gripping surface. In other words, the path may be free of a vertical movement or component relative to the opposing jaw, the site of interest and/or a point of reference.

At the end of translational movement, the opposing distal portions or tips, proximal portions, or both may be in contact with one another. At the end of translational movement, a gap may be defined between the opposing distal portions or tips, proximal portions, or both.

A non-translational movement may refer to one or more of the movements described herein, including any of the translational movements. A non-translational movement may refer to a movement where the opposing armatures, jaws, gripping surfaces, or a combination thereof are maintained in a generally non-parallel relationship relative to one another.

A non-translational movement may occur when the opposing jaws, griping surfaces, armatures, or a combination thereof are closer together than during a translational movement. Alternatively, a non-translational movement may occur when the opposing jaws, griping surfaces, armatures, or a combination thereof are father apart than during a translational movement, or vice versa.

During a non-translational movement, a distal portion of one of the armatures, jaws, and/or gripping surfaces may be moved towards or away from the opposing gripping surface while being simultaneously moved proximally relative to the distal portion of the other jaw. In other words, one of the jaws may move diagonally relative to the other jaw.

During a non-translational movement, one of the armatures, jaws, and/or gripping surfaces may be moved axially (e.g., distally, proximally, or both) relative to the introducer, the hand piece, or a reference point. During a non-translational movement, one or both of the armatures, jaws, and/or gripping surfaces may not be moved axially (e.g., distally, proximally, or both) relative to the introducer, the hand piece, or a reference point.

During a non-translational movement, one or both of the armatures, jaws, and/or gripping surfaces may move such that a gap defined between the distal portions closes faster than a gap defined between the proximal portions.

During a non-translational movement, one or both of the armatures, jaws, and/or gripping surfaces may be moved such that a gap defined between the proximal portions closes faster than a gap defined between the distal portions or tips.

During a non-translational movement, a distal portion or tip of one of the jaws or gripping surfaces may move along a path that is generally perpendicular to the opposing gripping surface. The path may be free of any movements or movement components along a path that is generally parallel to the gripping surface. In other words, the path may be free of a horizontal movement or component relative to the introducer, hand piece, and/or point of reference.

During a non-translational movement, a distal portion or tip of one of the jaws or gripping surfaces may move along a path that is generally parallel to the gripping surface of the opposing griping surface. The path may be free of any movements or movement components along a path that is generally perpendicular to the gripping surface. In other words, the path may be free of a vertical movement or component relative to the opposing jaw, the site of interest and/or a point of reference.

At the end of a non-translational movement, the opposing proximal portions may be in contact with one another while a gap is defined between the opposing distal portions or tips. At the end of a non-translational movement, the opposing distal portions or tips may be in contact with one another while a gap is defined between the opposing proximal portions. At the end of a non-translational movement, a gap defined between the opposing proximal portions may be taken up or non-existent. At the end of a non-translational movement, a gap defined between the opposing distal portions or tips may be taken up or nonexistent. At the end of a non-translational movement, the opposing proximal portions and the opposing distal portions may be in contact. At the end of a non-translational movement, the opposing proximal portions and the opposing distal portions may be spaced apart from one another.

The instrument may include a blade. The blade may function to effect an object or anatomical feature. The blade may be a cutting blade, scalpel, etc. The blade may be moved via one or more controls on the hand piece. The blade may be connected to an actuator, and moved by moving or actuating the actuator. The actuator that moves the blade may be the same actuator that moves one or both of the jaws, or may be a different actuator, rod, or mechanism. The blade may be located within the introducer and moved through the introducer. Movement of the blade may mean that the blade can be extended, retracted, reciprocated, rotated, or a combination thereof relative to one or both of the jaws, the hand piece, the floor, the patient or anatomy, about or along a longitudinal axis of the blade, introducer, actuator, or a combination thereof.

The blade may be extended beyond a distal end of the gripping assembly while the griping assembly is in a closed position, an open position, and/or in a positing therebetween. The blade may be electrically connected to a power source and used as a monopolar blade, a bipolar blade, or both. The blade may be electrically insulated to prevent electrical contact with one or more jaws. The blade may be electrically isolated from any power source and used a mechanical blade to non-electrically cut or transect an object or anatomical feature.

FIG. 1 illustrates an instrument 100. The instrument 100 includes a hand piece 102 and an introducer 104. A jaw assembly 10, illustrated schematically in this FIG, but illustrated in more detail in the following FIGS., extends distally from the hand piece 102. The instrument 100 includes a blade 18 and an actuator 16, both of which extend through the introducer 104. The instrument 100 includes controls 106a, 106b, 106c, 106d for operating the instrument 100, the jaw assembly 10, the blade 18, and the actuator 16. The instrument 100 can be connected to a power source 108 via one or more conductor wires 110 so that the instrument 100 can be used in electrosurgery.

Figure 2:
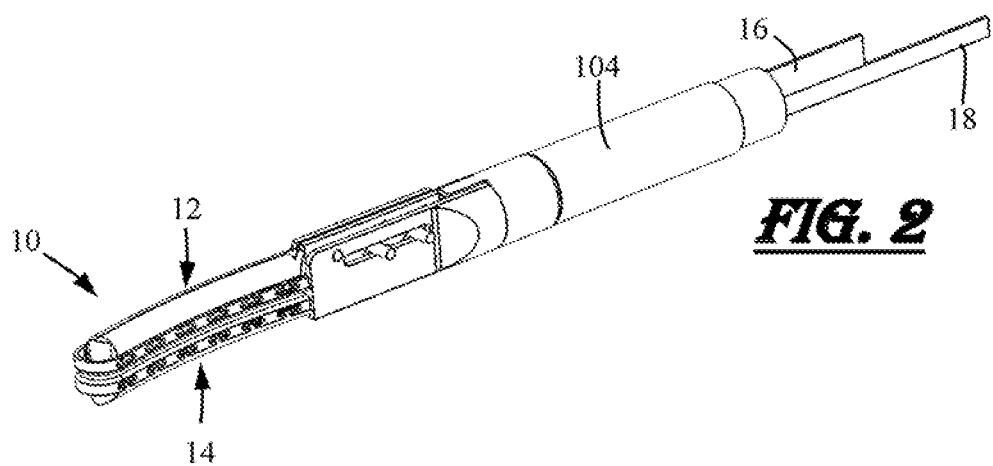
FIG. 2 is a perspective view of a jaw assembly.

FIG. 2 illustrates a jaw assembly 10. The jaw assembly 10 includes a pair of jaws comprising a first jaw 12 and a second jaw 14. The actuator 16 extends through the introducer 104, from the hand piece 120 (FIG. 1) to the jaw assembly 10. The blade 18 also extends through the introducer 104, from the hand piece 120 (FIG. 1) to the jaw assembly 10.

Figure 3:
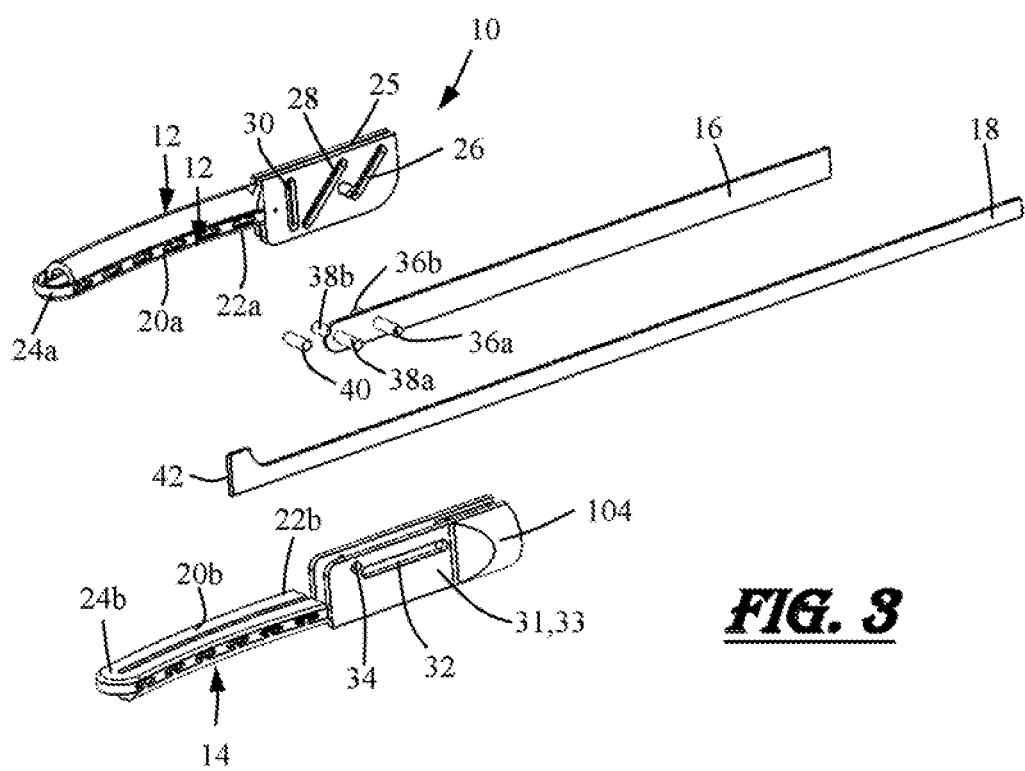
FIG. 3 is an exploded, perspective view of FIG. 2.

FIG. 3 is an exploded view of FIG. 2. The first jaw 12 includes a gripping face 20a that extends between a proximal portion 22a and a distal portion 24a. The first jaw 12 includes a proximal section 25 that includes a first slot 26, a second slot 28, and a third slot 30. The second jaw 14 includes a gripping face 20b that extends between a proximal portion 22b and a distal portion 24b. A proximal section 31 of the second jaw 14 or a distal section 33 of the introducer 104 includes a slot 32 and an aperture 34. The actuator 16 includes a pair of first pins 36a, 36b and a pair of second pins 38a, 38b. The jaw assembly 10 includes a pin 40. The blade 18 includes a cutting edge 42.

With continued reference to FIGS. 2 and 3, when the jaw assembly 10 is assembled, the first constraint comprises pin 36a received into slot 32 and pin 36b received into slot 26. The second constraint comprises pin 38a received into slot 32 and pin 38b received into slot 28. The third constraint comprises pin 40 received into aperture 34 and slot 30.

Figure 4:
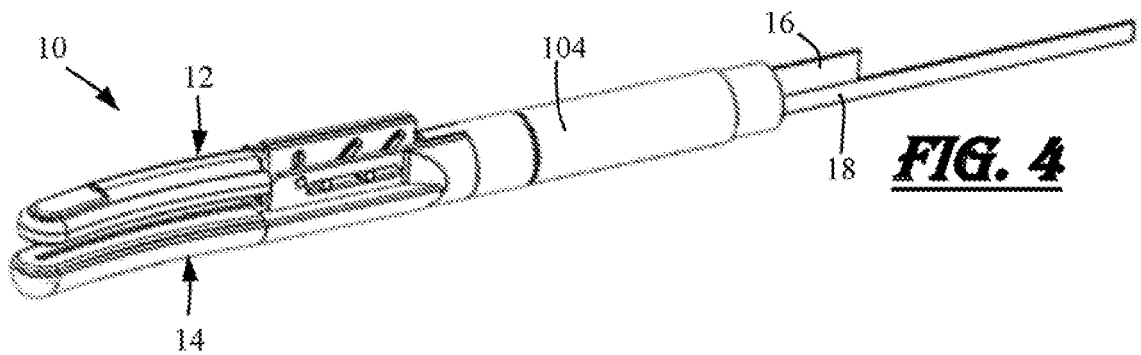
FIG. 4 is a perspective view of a jaw assembly.

FIG. 4 illustrates a jaw assembly 10. The jaw assembly 10 includes a pair of jaws comprising a first jaw 12 and a second jaw 14. The actuator 16 extends through the introducer 104, from the hand piece 120 (FIG. 1) to the jaw assembly 10. The blade 18 also extends through the introducer 104, from the hand piece 120 (FIG. 1) to the jaw assembly 10.

Figure 5:
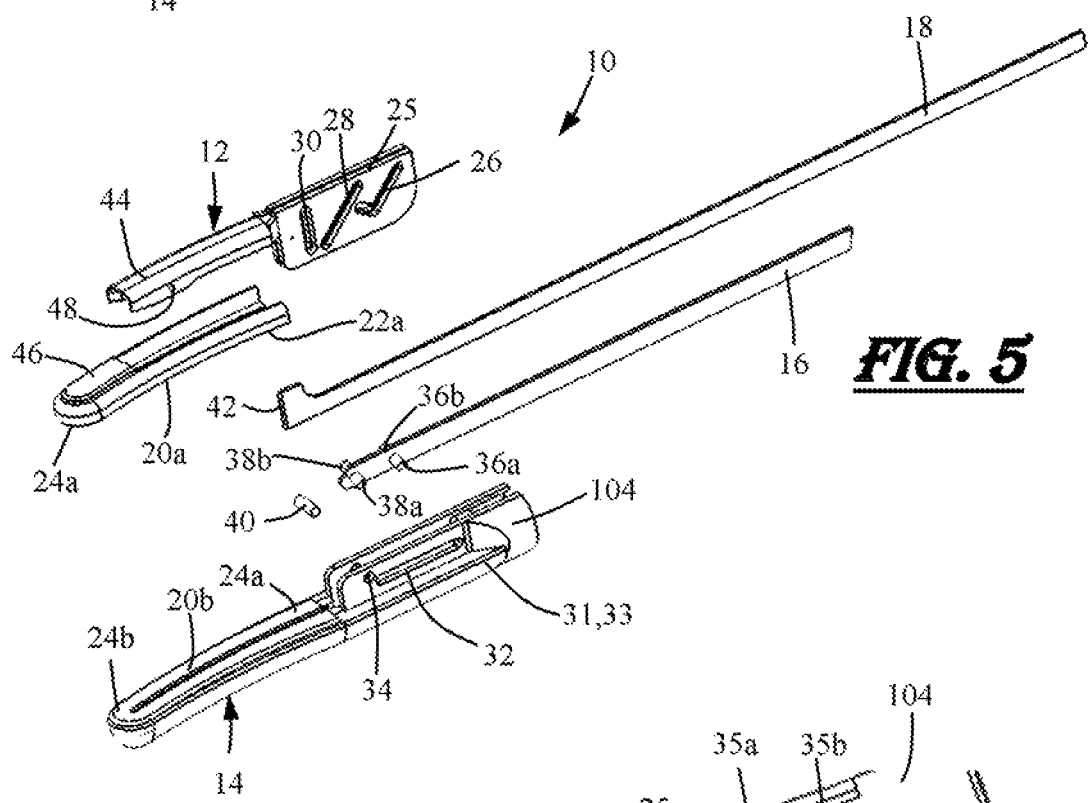
FIG. 5 is an exploded, perspective view of FIG. 4.

FIG. 5 is an exploded view of FIG. 4. The first jaw 12 includes a jaw armature 44 that is connected to a jaw portion 46 via a pivot 48 so that the first jaw 12 resembles a windshield wiper of an automobile, for example. The pivot 48 comprise a pin and a mating aperture or opening that so that the jaw portion 46 can rock or pivot or act like a seesaw about the pivot 48 relative to the armature 44. The jaw portion 46 includes a gripping face 20a comprising a proximal portion 22a and a distal portion 24a. A proximal section 25 of the armature 44 includes a first slot 26, a second slot 28, and a third slot 30. The second jaw 14 includes a gripping face 20b comprising a proximal portion 22b and a distal portion 24b. A proximal section 31 of the second jaw 14 or a distal section 33 of the introducer 104 includes a slot 32 and an aperture 34. The actuator 16 includes a pair of first pins 36a, 36b and a pair of second pins 38a, 38b. The jaw assembly 10 includes a pin 40. The blade 18 includes a cutting edge 42.

With continued reference to FIGS. 4 and 5, when the jaw assembly 10 is assembled, the first constraint comprises pin 36a received into slot 32 and pin 36b received into slot 26. The second constraint comprises pin 38a received into slot 32 and pin 38b received into slot 28. The third constraint comprises pin 40 received into aperture 34 and slot 30.

Figure 6:
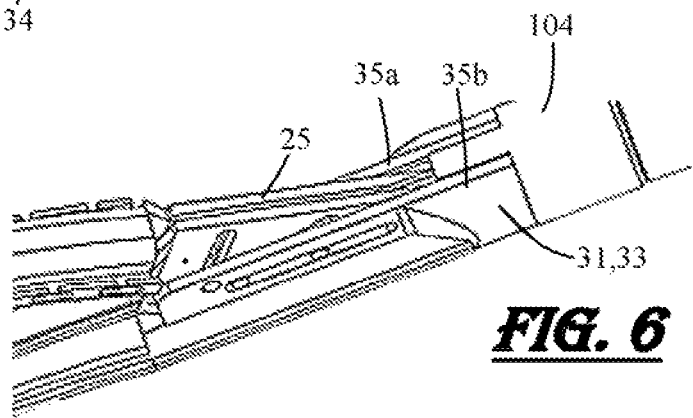
FIG. 6 is a partial perspective view of FIG. 4.

Referring now to FIG. 6, either the proximal section 31 of the second jaw 14 or a distal section 33 of the introducer 104 includes a first wall 35a and a spaced apart second wall 35b. The proximal section 25 of the first jaw 12 is received between the walls 35a, 35b. In another configuration, the proximal section 25 of the first jaw 12 may include opposing walls like the walls 35a, 35b, and may be in a staggered arrangement with walls 35a, 35b. This means that one wall of the proximal section 25 may be located outside of one of the walls 35a, 35b, while another wall of the proximal section 25 is located between the walls 35a, 35b. In yet another configuration, the proximal section 25 may include walls like the walls 35a, 35b, and either the proximal section 31 or the distal section 33 may include an end that resembles that of the proximal section 25.

Figure 7A:
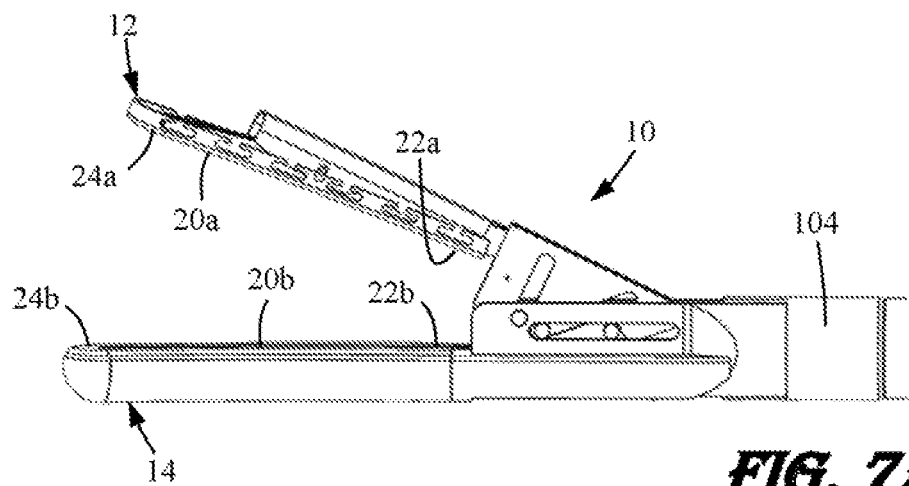
FIG. 7A is a side view of the jaw assembly of FIGS. 4-6.
Figure 7B:
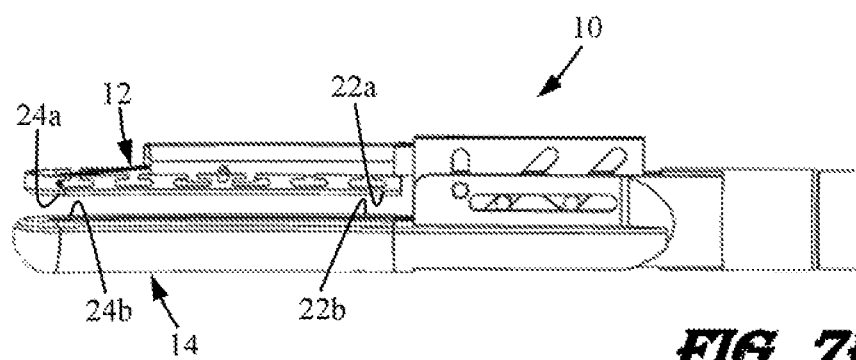
FIG. 7B is a side view of the jaw assembly of FIGS. 4-6.
Figure 7C:
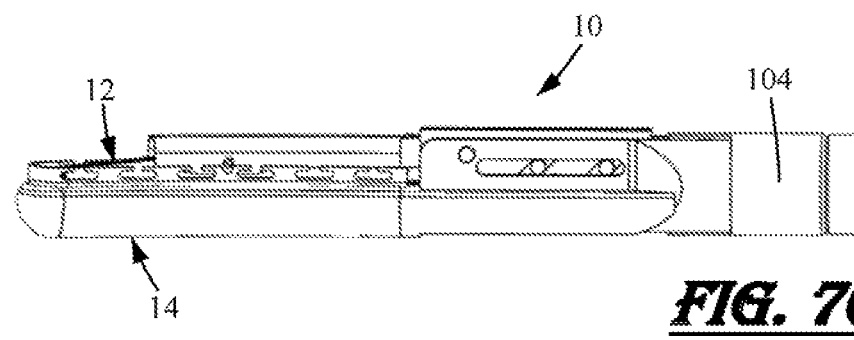
FIG. 7C is a side view of the jaw assembly of FIGS. 4-6.

FIGS. 7A-7C illustrate the jaw assembly 10 of FIGS. 4-6 moving between an open configuration (FIG. 7A) and a closed configuration (FIG. 7C). In the open configuration (FIG. 7A), the gripping faces 20a, 20b are spaced apart such that the opposing proximal portions 22a, 22b are closer together than the opposing distal portions 24a, 24b. By moving the actuator 16 proximally towards the hand piece 102 (FIG. 1), for example, by actuating the lever 106c, the jaw assembly 10 undergoes a non-translational movement where jaw 12 to moved towards the opposing jaw 14 until the gripping faces 20a, 20b are in a generally parallel arrangement such that a gap defined between the opposing proximal portions 22a, 22b is generally the same as a gap defined between the opposing distal portions 24a, 24b (See FIG. 7B). From the position in FIG. 7B, continued movement of the actuator 16 in the proximal direction causes the jaw assembly 10 to undergo a translational movement where the jaw 12 is moved towards jaw 14 such that opposing gripping faces 20a, 20b are brought into contact with one another in a generally parallel movement to the configuration illustrated in FIG. 7C.

Moving the actuator 16 in a distal direction away from the hand piece 102, for example, by actuating the lever 106c, causes jaw 12 to move away from jaw 14 along a translational path from the position illustrated in FIG. 7C to the position illustrated in FIG. 7B. Continued movement of the actuator 16 in a distal direction away from the hand piece 102 causes jaw 12 to then move away from jaw 14 along a non-translational path from the position illustrated in FIG. 7B to the position illustrated in FIG. 7A.

Figure 8:
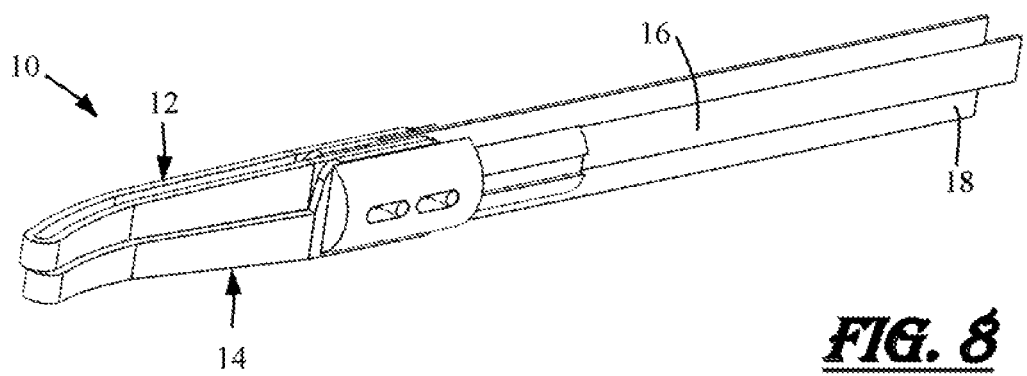
FIG. 8 is a perspective view of a jaw assembly.

FIG. 8 illustrates another jaw assembly 10 in the closed configuration; an actuator 16; and a blade 18. The jaw assembly 10 includes a pair of jaws comprising a first jaw 12 and a second jaw 14.

Figure 9:
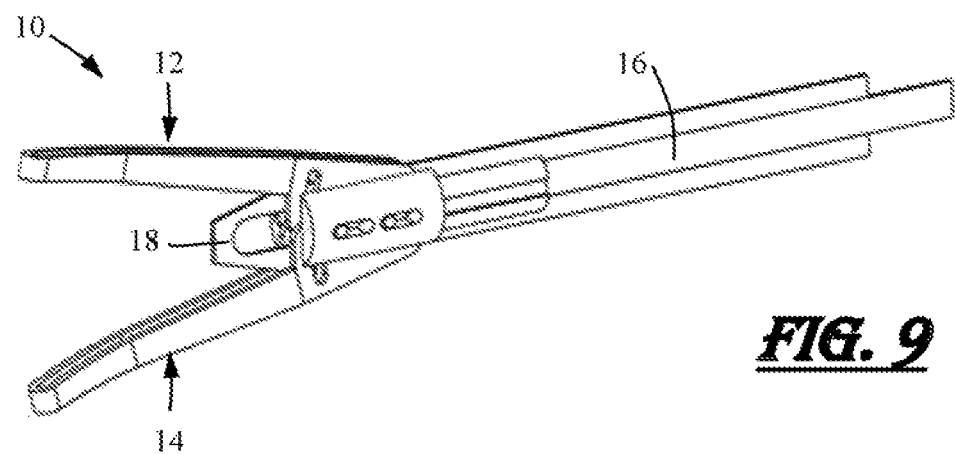
FIG. 9 is a perspective view of the jaw assembly of FIG. 8.

FIG. 9 illustrates the jaw assembly 10 of FIG. 8 in the open configuration.

Figure 10:
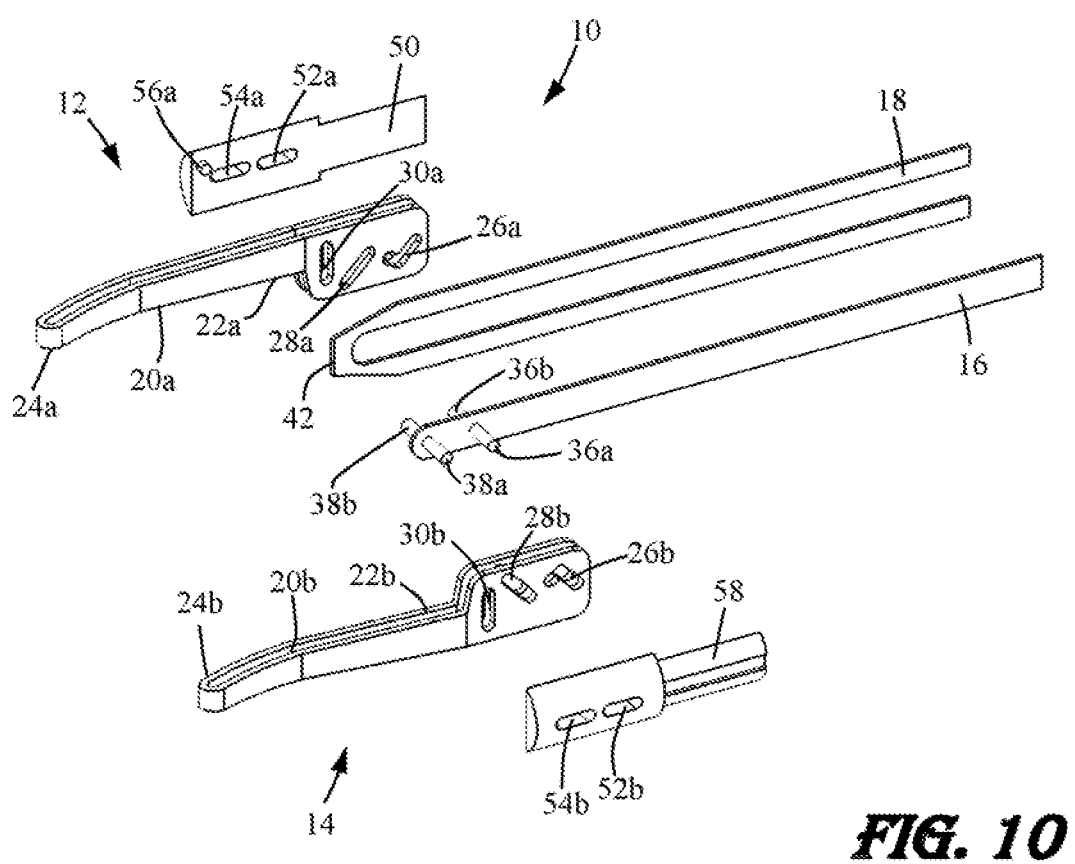
FIG. 10 is an exploded, perspective view of FIGS. 8 and 9.

FIG. 10 is an exploded view of FIGS. 8 and 9. The first jaw 12 includes a gripping face 20a comprising a proximal portion 22a and a distal portion 24a. The first jaw 12 includes a first slot 26a, a second slot 28a, and a third slot 30a. The first jaw 12 includes a first support member 50, which in some configurations may be a side wall of the introducer 104. The first support member 50 comprises a first slot 52a, a second slot 54a, and a first protrusion 56a. The first slot 52a and the second slot 54a may not be particularly necessary for the mechanism to move, but may add stability to the assembly.

The second jaw 14 includes a gripping face 20b comprising a proximal portion 22b and a distal portion 24b. The second jaw 14 includes a first slot 26b, a second slot 28b, and a third slot 30b. The second jaw 14 includes a second support member 58, which in some configurations may be a side wall of the introducer 104. The second support member 58 comprises a first slot 52b, a second slot 54b, and a second protrusion (not shown) that is substantially similar to the first protrusion 56a on the first support member 50. The first slot 52b and the second slot 54b may not be particularly necessary for the mechanism to move, but may add stability to the assembly. The actuator 16 includes a pair of first pins 36a, 36b and a pair of second pins 38a, 38b. The blade 18 includes a cutting edge 42.

With continued reference to FIGS. 8-10, when the jaw assembly 10 is assembled, the first constraint comprises pin 36a received into slots 26b and 52b, and pin 36b received into slots 26a and 52a. The second constraint comprises pin 38a received into slots 28b and 54b, and pin 38b received into slots 28a and 54a. The third constraint comprises protrusion 56a received into slot 30a and the protrusion (not shown) on the second link 58 received into slot 30b.

FIGS. 11A-11D illustrate a jaw assembly 10 moving between an open configuration and a closed configuration. The movement of the jaw assembly 10 shown in FIGS. 11A-11D may be the same as the movement of the jaw assembly 10 illustrated in FIGS. 8-10. In FIGS. 11A-11D, the support member 50 has been removed so that movement of the actuator 16 can be better illustrated.

Figure 11A:
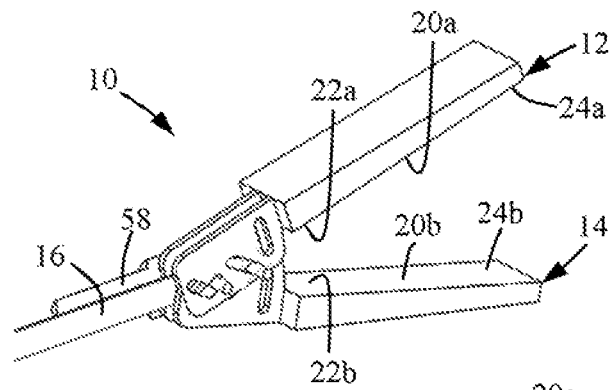
FIG. 11A is a perspective view of a jaw assembly.
Figure 11B:
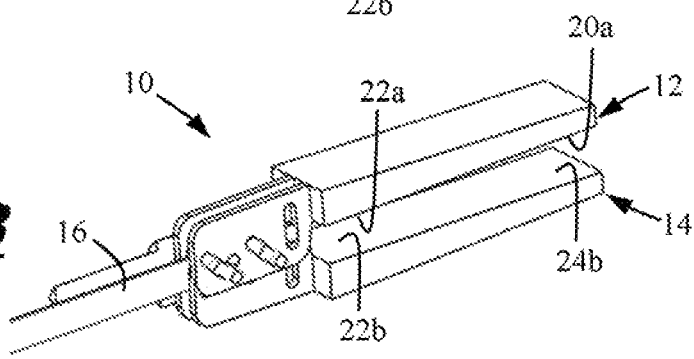
FIG. 11B is a perspective view of the jaw assembly of FIG. 11A.
Figure 11C:
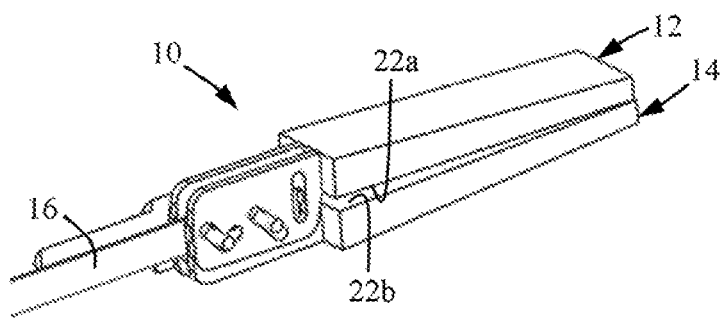
FIG. 11C is a perspective view of the jaw assembly of FIGS. 11A-11B.
Figure 11D:
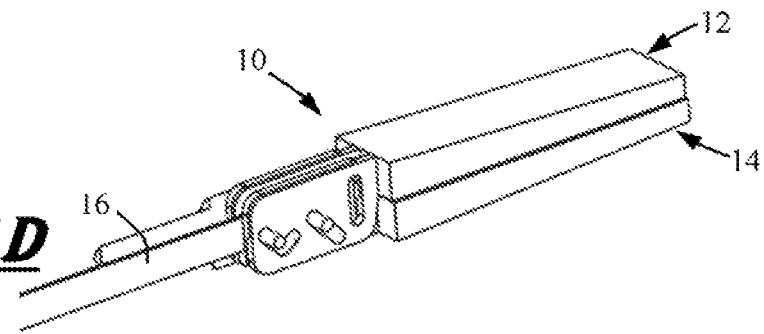
FIG. 11D is a perspective view of the jaw assembly of FIGS. 11A-11C.

In the open configuration (FIG. 11A), the gripping faces 20a, 20b are spaced apart such that the opposing proximal portions 22a, 22b are closer together than the opposing distal portions 24a, 24b. When the actuator is moved in a proximal direction towards the hand piece 102, for example by actuating the lever 106c, the jaw assembly 10 undergoes a non-translational movement until the gripping faces 20a, 20b are in a generally parallel arrangement such that a gap defined between the opposing proximal portions 22a, 22b is generally the same as a gap defined between the opposing distal portions 24a, 24b (FIG. 11B). The jaw assembly 10 then undergoes a translational movement where the jaws 12, 14 are moved in a parallel relative to one another as shown in FIG. 11B. From the position in FIG. 11B, continued movement of the actuator 16 in the proximal direction causes the jaw assembly 10 to undergo a non-translational movement such that the opposing distal portions 20a, 20b contact each other or are closer together than the opposing proximal portions 22a, 22b. From the position in FIG. 11C, continued movement of the actuator 16 in the proximal direction causes the jaw assembly 10 to undergo a second non-translational movement where the proximal portions 22a, 22b are brought closer together or into contact with each other as shown in FIG. 11D.

The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. An instrument, comprising: a) a hand piece; b) an introducer extending from the hand piece; c) a pair of jaws extending from the introducer, the pair of jaws comprising a first jaw and a second jaw; d) an actuator in communication with both the hand piece and the pair of jaws; e) a first constraint comprising a first slot and a mating first pin, the first pin fixedly coupled to the actuator; f) a second constraint comprising a second slot and a mating second pin, the second pin fixedly coupled to the actuator; and g) a third constraint comprising a link that is pivotally connected at one end to the introducer and at the other end to the first jaw, wherein both of the first slot and the second slot are located on the first jaw.

2. The instrument of claim 1, wherein the first jaw includes a first jaw armature and a first jaw member configured to pivot on the first jaw armature, and wherein both of the first slot and the second slot are located on the first jaw armature.

3. The instrument of claim 2, wherein the link is pivotally connected to the introducer and to the first jaw.

4. The instrument of claim 1, wherein movement of the actuator causes the pair of jaws to move between an open configuration and a closed configuration, and
wherein during the movement from the open configuration to the closed configuration, the pair of jaws undergo a translational movement followed by a first non-translational movement.

5. The instrument of claim 4, wherein each of the jaws comprise a gripping surface, and during the translational movement, the gripping surfaces remain parallel relative to one another.

6. The instrument of claim 5, wherein during the translational movement, a distal portion of the first jaw is moved towards the gripping surface of the second jaw along an axis that is perpendicular to the gripping surface of the second jaw, and
wherein after the translational movement, the pair of jaws undergo the first non-translational movement where the distal portion of the first jaw is moved towards the gripping surface of the second jaw while simultaneously also being moved proximally relative to a distal portion of the second jaw.

7. The instrument of claim 6, wherein during the first non-translational movement, a gap defined between the distal portions of the jaws closes faster than a gap defined between proximal portions of the jaws, and
wherein the first non-translational movement is followed by a second-non-translational movement where one or both of the jaws are moved such that the gap defined between the proximal portions of the jaws closes faster than the gap defined between the distal portions of the jaws.

8. The instrument of claim 6, wherein at an end of the first non-translational movement, the distal portions of the jaws are in contact with one another while a gap is defined between proximal portions of the jaws, and
wherein the first non-translational movement is followed by a second-non-translational movement where one or both of the jaws are moved such that the gap defined between the proximal portions of the jaws is taken up.

9. The instrument of claim 5, wherein at the end of the first non-translational movement, distal portions of the jaws are in contact with one another while a gap is defined between proximal portions of the jaws, and
wherein the first non-translational movement is followed by a second-non-translational movement where one or both of the jaws are moved such that the gap defined between the proximal portions of the jaws is taken up.

10. An instrument, comprising: a) a hand piece; b) an introducer extending from the hand piece; c) a pair of jaws extending from the introducer, the pair of jaws comprising a first jaw and a second jaw; d) are actuator in communication with both the hand piece and the pair of jaws; e) a first constraint comprising a first slot and a mating first pin, the first pin fixedly coupled to the actuator, wherein the first slot is on the first jaw; f) a second constraint comprising a second slot and a mating second pin, the second pin fixedly coupled to the actuator, wherein the second slot is on the first jaw; and g) a third constraint comprising a third sot and a mating third pin, the third slot is on the actuator and the third pin is on one or both of the first jaw and the second jaw, or the third pin is on the introducer and the third slot is on the first jaw.

11. The instrument of claim 10, wherein movement of the actuator causes the pair of jaws to move between an open configuration and a closed configuration, wherein during the movement from the open configuration to the closed configuration, the pair of jaws undergo a translational movement over a first range of motion followed by a first non-translational movement over a second range of motion, wherein during the translational movement, one or both of the jaws are moved towards one another while remaining parallel relative to one another, and wherein during the first non-translational movement, one or both of the jaws are moved angularly towards one another.

12. The instrument of claim 10, wherein movement of the actuator causes the pair of jaws to move between an open configuration and a closed configuration, and wherein during the movement from the open configuration to the closed configuration, the pair of jaws undergo a translational movement followed by a first non-translational movement.

13. The instrument of claim 12, wherein each of the jaws comprise a gripping surface, and during the translational movement, the gripping surfaces remain parallel relative to one another.

14. The instrument of claim 13, wherein during the translational movement, a distal portion of the first jaw is moved towards the gripping surface of the second jaw along an axis that is perpendicular to the gripping surface of the second jaw, and wherein after the translational movement, the pair of jaws undergo the first non-translational movement where the distal portion of the first jaw is moved towards the gripping surface of the second jaw while simultaneously also being moved proximally relative to a distal portion of the second jaw.

15. The instrument of claim 14, wherein during the first non-translational movement, a gap defined between the distal portions of the jaws closes faster than a gap defined between proximal portions of the jaws, and wherein the first non-translational movement is followed by a second-non-translational movement where one or both of the pair of jaws are moved such that the gap defined between the proximal portions closes faster than the gap defined between the distal portions.

16. The instrument of claim 14, wherein at the end of the first non-translational movement, the distal portions of the jaws are in contact with one another while a gap is defined between proximal portions of the jaws, and wherein the first non-translational movement is followed by a second-non-translational movement where one or both of the pair of jaws are moved such that the gap defined between the proximal portions of the jaws is taken up.

17. An instrument, comprising:
 a) a hand piece;
 b) an introducer extending from the hand piece;
 c) a pair of jaws extending from the introducer, the pair of jaws comprising:
  i) a first jaw including a first jaw armature and a first gripping section; and
  i) a second jaw;
 d) an actuator in communication with both the hand piece and the pair of jaws;
 e) a first constraint comprising a first slot and a mating first pin;
 wherein the first slot is on the actuator and the first pin is on the first jaw armature;
 f) a second constraint comprising a second slot and a mating second pin;
 wherein the second slot is on the actuator and the second pin is on the first jaw-armature; and
 g) a third constraint comprising a third slot and a mating third pin,
 wherein the third pin is on the introducer and the third slot is on the first jaw armature, and
 wherein the third constraint restrains movement of the first jaw armature relative to the actuator.

* * * * *

UNITED STATES PATENT AND TRADEMARK OFFICE
CERTIFICATE OF CORRECTION

PATENT NO. : 10,792,060 B2
APPLICATION NO. : 15/902113
DATED : October 6, 2020
INVENTOR(S) : Batchelor et al.

Page 1 of 1

It is certified that error appears in the above-identified patent and that said Letters Patent is hereby corrected as shown below:

In the Claims

In Column 24, Line 57, in Claim 10, delete "are" and insert --an-- therefor

In Column 24, Line 64, in Claim 10, delete "sot" and insert --slot-- therefor

In Column 26, Line 22, in Claim 17, delete "i)" and insert --ii)-- therefor

Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*